(12) United States Patent
Lim et al.

(10) Patent No.: US 12,303,555 B2
(45) Date of Patent: May 20, 2025

(54) TARGETING OF MELANOCYTES FOR DELIVERING THERAPEUTIC OR DIAGNOSTIC AGENTS USING PROTEIN NANOCAGES

(71) Applicants: NANYANG TECHNOLOGICAL UNIVERSITY, Singapore (SG); NATIONAL SKIN CENTER (S) PTE LTD, Singapore (SG)

(72) Inventors: Sierin Lim, Singapore (SG); Sathyamoorthy Bhaskar, Singapore (SG); Steven Thng, Singapore (SG); Ambili Kuniyil, Singapore (SG); Sarker Mridul, Singapore (SG)

(73) Assignees: NANYANG TECHNOLOGICAL UNIVERSITY, Singapore (SG); NATIONAL SKIN CENTER (S) PTE LTD, Singapore (SG)

( * ) Notice: Subject to any disclaimer, the term of this patent is extended or adjusted under 35 U.S.C. 154(b) by 578 days.

(21) Appl. No.: 17/525,804

(22) Filed: Nov. 12, 2021

(65) Prior Publication Data

US 2022/0062387 A1    Mar. 3, 2022

Related U.S. Application Data

(63) Continuation of application No. 15/514,134, filed as application No. PCT/SG2015/050343 on Sep. 25, 2015, now Pat. No. 11,202,820.

(30) Foreign Application Priority Data

Sep. 25, 2014   (SG) .......................... 10201406072V

(51) Int. Cl.
| | | |
|---|---|---|
| *A61K 38/34* | (2006.01) | |
| *A61K 9/00* | (2006.01) | |
| *A61K 38/35* | (2006.01) | |
| *A61K 47/10* | (2017.01) | |
| *A61P 17/00* | (2006.01) | |
| *C07K 14/195* | (2006.01) | |
| *C07K 14/32* | (2006.01) | |
| *C07K 14/47* | (2006.01) | |
| *C07K 14/685* | (2006.01) | |
| *C07K 14/69* | (2006.01) | |
| *C07K 14/695* | (2006.01) | |
| *C07K 14/72* | (2006.01) | |
| *B82Y 5/00* | (2011.01) | |

(52) U.S. Cl.
CPC ............ *A61K 38/34* (2013.01); *A61K 9/0014* (2013.01); *A61K 38/35* (2013.01); *A61K 47/10* (2013.01); *A61P 17/00* (2018.01); *C07K 14/195* (2013.01); *C07K 14/32* (2013.01); *C07K 14/47* (2013.01); *C07K 14/685* (2013.01); *C07K 14/69* (2013.01); *C07K 14/695* (2013.01); *C07K 14/723* (2013.01); *B82Y 5/00* (2013.01); *C12Y 102/04001* (2013.01)

(58) Field of Classification Search
CPC ....... A61K 38/34; A61K 9/0014; A61P 17/00; C07K 14/32; C07K 14/47; C07K 14/685; C07K 14/69; C07K 14/695
See application file for complete search history.

(56) References Cited

U.S. PATENT DOCUMENTS

| | | | |
|---|---|---|---|
| 4,469,774 | A | 9/1984 | Lee |
| 5,505,931 | A | 4/1996 | Pribish |
| 5,563,250 | A | 10/1996 | Hylarides et al. |
| 5,767,288 | A | 6/1998 | Rock et al. |
| 8,791,062 | B2 | 7/2014 | Hsu et al. |
| 2007/0258889 | A1 | 11/2007 | Douglas et al. |
| 2012/0128756 | A1 | 5/2012 | Hsu et al. |

FOREIGN PATENT DOCUMENTS

| | | |
|---|---|---|
| WO | 87/04623 A1 | 8/1987 |
| WO | 03/094849 A2 | 11/2003 |
| WO | 2007/113531 A2 | 10/2007 |
| WO | 2009/095857 A1 | 8/2009 |
| WO | 2012/064429 A2 | 5/2012 |
| WO | 2014/031727 A1 | 2/2014 |
| WO | 2015/135597 A1 | 9/2015 |

OTHER PUBLICATIONS

Vannucci et al. 2012 (Selective targeting of melanoma by PEG-masked protein-based multifunctional nanoparticles; International Journal of Nanomedicine 2012(7):1489-1509). (Year: 2012).*
Bandyopadhyay, "Topical treatment of melisma," *Indian Journal of Dermatology* 54(4):303-309, 2009.
Bard, "Malignant Melanoma: Targeting Strategies Based On α-Melanocyte Stimulating Hormone: A Review," *Inflammopharmacology* 3:7-23, 1995.
Buecheler et al., "Development of a protein nanoparticle platform for targeting EGFR expressing cancer cells," *J Chem Technol Biotechnol* 90:1230-1236, 2015.
Carlson et al., "Melanocyte Receptors: Clinical Implications and Therapeutic Relevance," *Dermatol Clin.* 25(4):541-ix, 2007, 22 pages.

(Continued)

*Primary Examiner* — Mary Maille Lyons
(74) *Attorney, Agent, or Firm* — Seed IP Law Group LLP

(57) ABSTRACT

The present invention relates to protein nanocages comprising a melanocyte-targeting moiety and pharmaceutical compositions comprising the protein cages as well as methods for treating or diagnosing hyperpigmentation disorders or other melanocyte-related disorders using the protein nanocages or pharmaceutical compositions.

11 Claims, 5 Drawing Sheets

Specification includes a Sequence Listing.

(56) References Cited

OTHER PUBLICATIONS

Dalmau et al., "Thermostability and Molecular Encapsulation Within an Engineered Caged Protein Scaffold," *Biotechnology and Bioengineering* 101(4):654-664, 2008.

Domingo et al., "Multiple Display of Peptides and Proteins on a Macromolecular Scaffold Derived from a Multienzyme Complex," *Journal of Molecular Biology* 305:259-267, 2001.

Eberle et al., "Radiolabeled α-melanocyte-stimulating hormone analogs for receptor-mediated targeting of melanoma: from tritium to indium," *Journal of Molecular Recognition* 16:248-254, 2003.

Extended European Search Report, dated Feb. 15, 2018, for European Application No. 15843793.9-1120 / 3197920, 9 pages.

Fantechi et al., "A Smart Platform for Hyperthermia Application in Cancer Treatment: Cobalt-Doped Ferrite Nanoparticles Mineralized in Human Ferritin Cages," *ACS Nano* 8(5):4705-4719, 2014.

Flenniken et al., "Selective attachment and release of a chemotherapeutic agent from the interior of a protein cage architecture," *Chem. Commun.* 4:447-449, 2005.

Froidevaux et al., "Melanoma Targeting with DOTA-α-Melanocyte-Stimulating Hormone Analogs: Structural Parameters Affecting Tumor Uptake and Kidney Uptake," *J Nucl Med* 46:887-895, 2005.

Ghanem et al., "Human melanoma targeting with α-MSH-melphalan conjugate," *Melanoma Research* 1:105-114, 1991.

Greenspan et al., "Defining epitopes: It's not as easy as it seems," *Nature Biotechnology* 17:936-937, Oct. 1999.

Guo et al., "Melanoma targeting property of a Lu-177-labeled lactam bridge-cyclized alpha-MSH peptide," *Bioorganic & Medicinal Chemistry Letters* 23:2319-2323, 2013.

Ho et al., "The Asian Dermatologic Patient," *Am J Clin Dermatol* 10(3):153-168, 2009.

Miao et al., "Alpha-melanocyte stimulating hormone peptide-targeted melanoma imaging," *Frontiers in Bioscience* 12:4514-4524, 2007.

Milne et al., "Molecular architecture and mechanism of an icosahedral pyruvate dehydrogenase complex: a multifunctional catalytic machine," *The EMBO Journal* 21(21):5587-5598, 2002.

Olney et al., "Targeting central melanocortin receptors: a promising novel approach for treating alcohol abuse disorders," *Frontiers in Neuroscience* 8(128): 2014, 9 pages.

Paramelle et al., "Specific Internalisation of Gold Nanoparticles into Engineered Porous Protein Cages via Affinity Binding," *PLoS ONE*, Sep. 13, 2016. (14 pages).

Paudel et al., "Challenges and opportunities in dermal/transdermal delivery," *Therapeutic Delivery* 1(1):109-131, 2010.

Peng et al., "Design of a reversible inversed pH-responsive caged protein," *Biomater. Sci.*, 3:627-635 (2015).

Peng et al., "Designing Non-Active Iron-Binding Site on a Protein Cage for Biological Synthesis of Nanoparticles," *Small* 10(15):3131-3138 (2014).

Peng et al., "Trimer-Based Design of pH-Responsive Protein Cage Results in Soluble Disassembled Structures," *Biomacromolecules* 12:3131-3138, 2011.

Prokop et al. (eds.), *Intracellular Delivery II*, Springer, New York, NY, 2014, Vannucci et al., "Multifunctional Protein-Based Nanoparticles for Cancer Theranosis," pp. 231-253. (24 pages).

Ren et al., "Biomimetic Design of Protein Nanomaterials for Hydrophobic Molecular Transport," *Advanced Functional Materials* 22:3170-3180, 2012.

Ren et al., "Engineered drug-protein nanoparticle complexes for folate receptor targeting," *Biochemical Engineering Journal* 89:33-41, 2014.

Ren et al., "Protein Nanocapsules Containing Doxorubicin as a pH-Responsive Delivery System," *Small* 7(8):1051-1060, 2011.

Sana et al., "A manganese-ferritin nanocomposite as an ultrasensitive $T_2$ contrast agent," *Chem. Commun.* 48:862-864, 2012.

Sana et al., "Iron-based ferritin nanocore as a contrast agent," *Biointerphases* 5(3):FA48-FA52, 2010.

Ubeid et al., "Minireview: Peptide Analogs and Short Sequence Oligopeptides as Modulators of Skin Pigmentation," *Current Topics in Medicinal Chemistry* 14:1418-1424, 2014.

Vannucci et al., "Selective targeting of melanoma by PEG-masked protein-based multifunctional nanoparticles," *International Journal of Nanomedicine* 7:1489-1509, 2012.

Walsh et al., "MRI contrast demonstration of antigen-specific targeting with an iron-based ferritin construct," *J Nanopart Res* 15:1409, 2013, 10 pages.

Willner et al., "(6-Maleimidocaproyl) hydrazone of Doxorubicin—A New Derivative for the Preparation of Immunoconjugates of Doxorubicin," *Bioconjugate Chem.* 4:521-527, 1993.

Yamaguchi et al., "Melanocytes and Their Diseases," *Cold Spring Harb Perspect Med* 4:a017046, 2014, 19 pages.

Zhen et al., "RGD-Modified Apoferritin Nanoparticles for Efficient Drug Delivery to Tumors," *ACS Nano* 7(6):4830-4837, 2013.

* cited by examiner

SEQUENCE LISTING

```
<160> NUMBER OF SEQ ID NOS: 16

<210> SEQ ID NO 1
<211> LENGTH: 260
<212> TYPE: PRT
<213> ORGANISM: Bacillus stearothermophilus

<400> SEQUENCE: 1

Met Leu Ser Val Pro Gly Pro Ala Ala Ala Glu Glu Lys Ala Ala Pro
1               5                   10                  15

Ala Ala Ala Lys Pro Ala Thr Thr Glu Gly Glu Phe Pro Glu Thr Arg
                20                  25                  30

Glu Lys Met Ser Gly Ile Arg Arg Ala Ile Ala Lys Ala Met Val His
            35                  40                  45

Ser Lys His Thr Ala Pro His Val Thr Leu Met Asp Glu Ala Asp Val
        50                  55                  60

Thr Lys Leu Val Ala His Arg Lys Lys Phe Lys Ala Ile Ala Ala Glu
65                  70                  75                  80

Lys Gly Ile Lys Leu Thr Phe Leu Pro Tyr Val Val Lys Ala Leu Val
                85                  90                  95

Ser Ala Leu Arg Glu Tyr Pro Val Leu Asn Thr Ser Ile Asp Asp Glu
                100                 105                 110

Thr Glu Glu Ile Ile Gln Lys His Tyr Tyr Asn Ile Gly Ile Ala Ala
            115                 120                 125

Asp Thr Asp Arg Gly Leu Leu Val Pro Val Ile Lys His Ala Asp Arg
        130                 135                 140

Lys Pro Ile Phe Ala Leu Ala Gln Glu Ile Asn Glu Leu Ala Glu Lys
145                 150                 155                 160

Ala Arg Asp Gly Lys Leu Thr Pro Gly Glu Met Lys Gly Ala Ser Cys
                165                 170                 175

Thr Ile Thr Asn Ile Gly Ser Ala Gly Gly Gln Trp Phe Thr Pro Val
            180                 185                 190

Ile Asn His Pro Glu Val Ala Ile Leu Gly Ile Gly Arg Ile Ala Glu
        195                 200                 205

Lys Pro Ile Val Arg Asp Gly Glu Ile Val Ala Ala Pro Met Leu Ala
    210                 215                 220

Leu Ser Leu Ser Phe Asp His Arg Met Ile Asp Gly Ala Thr Ala Gln
225                 230                 235                 240

Lys Ala Leu Asn His Ile Lys Arg Leu Leu Ser Asp Pro Glu Leu Leu
                245                 250                 255

Leu Met Glu Ala
            260

<210> SEQ ID NO 2
<211> LENGTH: 260
<212> TYPE: PRT
<213> ORGANISM: Bacillus stearothermophilus
```

<400> SEQUENCE: 2

Met Leu Ser Val Pro Gly Pro Ala Ala Glu Glu Lys Ala Ala Pro
1               5                   10                  15

Ala Ala Ala Lys Pro Ala Thr Thr Glu Gly Glu Phe Pro Glu Thr Arg
            20                  25                  30

Glu Lys Met Ser Gly Ile Arg Arg Ala Ile Ala Lys Ala Met Val His
        35                  40                  45

Ser Lys His Thr Ala Pro His Val Thr Leu Met Asp Glu Ala Asp Val
    50                  55                  60

Thr Lys Leu Val Ala His Arg Lys Lys Phe Lys Ala Ile Ala Ala Glu
65                  70                  75                  80

Lys Gly Ile Lys Leu Thr Phe Leu Pro Tyr Val Val Lys Ala Leu Val
                85                  90                  95

Ser Ala Leu Arg Glu Tyr Pro Val Leu Asn Thr Ser Ile Asp Asp Glu
            100                 105                 110

Thr Glu Glu Ile Ile Gln Lys His Tyr Tyr Asn Ile Gly Ile Ala Ala
        115                 120                 125

Asp Thr Asp Arg Gly Leu Leu Val Pro Val Ile Lys His Ala Asp Arg
    130                 135                 140

Lys Pro Ile Phe Ala Leu Ala Gln Glu Ile Asn Glu Leu Ala Glu Lys
145                 150                 155                 160

Ala Arg Asp Gly Lys Leu Thr Pro Gly Glu Met Lys Gly Ala Ser Cys
                165                 170                 175

Thr Ile Thr Asn Ile Gly Ser Ala Gly Gly Gln Trp Phe Thr Pro Val
            180                 185                 190

Ile Asn His Pro Glu Val Ala Ile Leu Gly Ile Gly Arg Ile Ala Glu
        195                 200                 205

Lys Pro Ile Val Arg Cys Cys Glu Ile Val Ala Ala Pro Met Leu Ala
    210                 215                 220

Leu Ser Leu Ser Phe Asp His Arg Met Ile Asp Gly Ala Thr Ala Gln
225                 230                 235                 240

Lys Ala Leu Asn His Ile Lys Arg Leu Leu Ser Asp Pro Glu Leu Leu
                245                 250                 255

Leu Met Glu Ala
            260

<210> SEQ ID NO 3
<211> LENGTH: 173
<212> TYPE: PRT
<213> ORGANISM: Archaeoglobus fulgidus

<400> SEQUENCE: 3

Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
        35                  40                  45

Trp Gln Glu Glu Leu Met His Ala Met Lys Met Phe Asp Phe Val Ser
    50                  55                  60

Glu Arg Gly Gly Arg Val Lys Leu Tyr Ala Val Glu Glu Pro Pro Ser
65                  70                  75                  80

Glu Trp Asp Ser Pro Leu Ala Ala Phe Glu His Val Tyr Glu His Glu
                85                  90                  95

```
Val Asn Val Thr Lys Arg Ile His Glu Leu Val Glu Met Ala Met Gln
            100                 105                 110

Glu Lys Asp Phe Ala Thr Tyr Asn Phe Leu Gln Trp Tyr Val Ala Glu
            115                 120                 125

Gln Val Glu Glu Ala Ser Ala Leu Asp Ile Val Glu Lys Leu Arg
        130                 135                 140

Leu Ile Gly Glu Asp Lys Arg Ala Leu Leu Phe Leu Asp Lys Glu Leu
145                 150                 155                 160

Ser Leu Arg Gln Phe Thr Pro Pro Ala Glu Glu Lys
                165                 170
```

<210> SEQ ID NO 4
<211> LENGTH: 170
<212> TYPE: PRT
<213> ORGANISM: Archaeoglobus fulgidus

<400> SEQUENCE: 4

```
Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
            35                  40                  45

Trp Gln Glu Glu Leu Met His Ala Met Lys Met Phe Asp Phe Val Ser
50                  55                  60

Glu Arg Gly Gly Arg Val Lys Leu Tyr Ala Val Glu Glu Pro Pro Ser
65                  70                  75                  80

Glu Trp Asp Ser Pro Leu Ala Ala Phe Glu His Val Tyr Glu His Glu
                85                  90                  95

Val Asn Val Thr Lys Arg Ile His Glu Leu Val Glu Met Ala Met Gln
            100                 105                 110

Glu Lys Asp Phe Ala Thr Tyr Asn Phe Leu Gln Trp Tyr Val Ala Glu
            115                 120                 125

Gln Val Glu Glu Ala Ser Ala Leu Asp Ile Val Glu Lys Leu Arg
        130                 135                 140

Leu Ile Gly Glu Asp Ala Ala Leu Leu Phe Leu Asp Lys Glu Leu
145                 150                 155                 160

Ser Leu Arg Gln Phe Thr Pro Pro Ala Glu
                165                 170
```

<210> SEQ ID NO 5
<211> LENGTH: 183
<212> TYPE: PRT
<213> ORGANISM: Homo sapiens

<400> SEQUENCE: 5

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
50                  55                  60

Glu His Ala Glu Lys Leu Met Lys Leu Gln Asn Gln Arg Gly Gly Arg
65                  70                  75                  80
```

```
Ile Phe Leu Gln Asp Ile Lys Lys Pro Asp Cys Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 6
<211> LENGTH: 175
<212> TYPE: PRT
<213> ORGANISM: Homo sapiens

<400> SEQUENCE: 6

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175

<210> SEQ ID NO 7
<211> LENGTH: 13
<212> TYPE: PRT
<213> ORGANISM: Artificial sequence
<220> FEATURE:
<223> OTHER INFORMATION: Synthetic construct

<400> SEQUENCE: 7

Ser Tyr Ser Met Glu His Phe Arg Trp Gly Lys Pro Val
1               5                   10

<210> SEQ ID NO 8
<211> LENGTH: 22
<212> TYPE: PRT
```

<213> ORGANISM: Artificial sequence
<220> FEATURE:
<223> OTHER INFORMATION: Synthetic construct

<400> SEQUENCE: 8

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 9
<211> LENGTH: 12
<212> TYPE: PRT
<213> ORGANISM: Artificial sequence
<220> FEATURE:
<223> OTHER INFORMATION: Synthetic construct

<400> SEQUENCE: 9

Tyr Val Met Gly His Phe Arg Trp Asp Arg Phe Gly
1               5                   10

<210> SEQ ID NO 10
<211> LENGTH: 38
<212> TYPE: PRT
<213> ORGANISM: Artificial sequence
<220> FEATURE:
<223> OTHER INFORMATION: Synthetic construct

<400> SEQUENCE: 10

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu
        35

<210> SEQ ID NO 11
<211> LENGTH: 11
<212> TYPE: PRT
<213> ORGANISM: Artificial sequence
<220> FEATURE:
<223> OTHER INFORMATION: Synthetic construct

<400> SEQUENCE: 11

Ala Cys Thr Gly Ser Thr Gln His Gln Cys Gly
1               5                   10

<210> SEQ ID NO 12
<211> LENGTH: 11
<212> TYPE: PRT
<213> ORGANISM: Artificial sequence
<220> FEATURE:
<223> OTHER INFORMATION: Synthetic construct

<400> SEQUENCE: 12

Ala Cys His Ser Ala Leu Thr Lys His Cys Gly
1               5                   10

<210> SEQ ID NO 13
<211> LENGTH: 11
<212> TYPE: PRT
<213> ORGANISM: Artificial sequence
<220> FEATURE:
<223> OTHER INFORMATION: Synthetic construct

<400> SEQUENCE: 13

Ala Cys Lys Thr Gly Ser His Asn Gln Cys Gly
1               5                   10

<210> SEQ ID NO 14
<211> LENGTH: 275
<212> TYPE: PRT
<213> ORGANISM: Bacillus stearothermophilus

<400> SEQUENCE: 14

Met Ala Cys Thr Gly Ser Thr Gln His Gln Cys Gly Gly Gly Ser
1               5                   10                  15

Leu Ser Val Pro Gly Pro Ala Ala Glu Glu Lys Ala Ala Pro Ala
                20                  25                  30

Ala Ala Lys Pro Ala Thr Thr Glu Gly Glu Phe Pro Glu Thr Arg Glu
            35                  40                  45

Lys Met Ser Gly Ile Arg Arg Ala Ile Ala Lys Ala Met Val His Ser
        50                  55                  60

Lys His Thr Ala Pro His Val Thr Leu Met Asp Glu Ala Asp Val Thr
65                  70                  75                  80

Lys Leu Val Ala His Arg Lys Lys Phe Lys Ala Ile Ala Ala Glu Lys
                85                  90                  95

Gly Ile Lys Leu Thr Phe Leu Pro Tyr Val Val Lys Ala Leu Val Ser
                100                 105                 110

Ala Leu Arg Glu Tyr Pro Val Leu Asn Thr Ser Ile Asp Asp Glu Thr
            115                 120                 125

Glu Glu Ile Ile Gln Lys His Tyr Tyr Asn Ile Gly Ile Ala Ala Asp
130                 135                 140

Thr Asp Arg Gly Leu Leu Val Pro Val Ile Lys His Ala Asp Arg Lys
145                 150                 155                 160

Pro Ile Phe Ala Leu Ala Gln Glu Ile Asn Glu Leu Ala Glu Lys Ala
                165                 170                 175

Arg Asp Gly Lys Leu Thr Pro Gly Glu Met Lys Gly Ala Ser Cys Thr
            180                 185                 190

Ile Thr Asn Ile Gly Ser Ala Gly Gly Gln Trp Phe Thr Pro Val Ile
        195                 200                 205

Asn His Pro Glu Val Ala Ile Leu Gly Ile Gly Arg Ile Ala Glu Lys
    210                 215                 220

Pro Ile Val Arg Cys Cys Glu Ile Val Ala Ala Pro Met Leu Ala Leu
225                 230                 235                 240

Ser Leu Ser Phe Asp His Arg Met Ile Asp Gly Ala Thr Ala Gln Lys
                245                 250                 255

Ala Leu Asn His Ile Lys Arg Leu Leu Ser Asp Pro Glu Leu Leu Leu
            260                 265                 270

Met Glu Ala
        275

<210> SEQ ID NO 15
<211> LENGTH: 275
<212> TYPE: PRT
<213> ORGANISM: Bacillus stearothermophilus

<400> SEQUENCE: 15

Met Ala Cys His Ser Ala Leu Thr Lys His Cys Gly Gly Gly Ser
1               5                   10                  15

Leu Ser Val Pro Gly Pro Ala Ala Ala Glu Glu Lys Ala Ala Pro Ala
                20                  25                  30

Ala Ala Lys Pro Ala Thr Thr Glu Gly Glu Phe Pro Glu Thr Arg Glu
             35                  40                  45

Lys Met Ser Gly Ile Arg Arg Ala Ile Ala Lys Ala Met Val His Ser
     50                  55                  60

Lys His Thr Ala Pro His Val Thr Leu Met Asp Glu Ala Asp Val Thr
 65                  70                  75                  80

Lys Leu Val Ala His Arg Lys Lys Phe Lys Ala Ile Ala Ala Glu Lys
                 85                  90                  95

Gly Ile Lys Leu Thr Phe Leu Pro Tyr Val Val Lys Ala Leu Val Ser
             100                 105                 110

Ala Leu Arg Glu Tyr Pro Val Leu Asn Thr Ser Ile Asp Asp Glu Thr
             115                 120                 125

Glu Glu Ile Ile Gln Lys His Tyr Tyr Asn Ile Gly Ile Ala Ala Asp
130                 135                 140

Thr Asp Arg Gly Leu Leu Val Pro Val Ile Lys His Ala Asp Arg Lys
145                 150                 155                 160

Pro Ile Phe Ala Leu Ala Gln Glu Ile Asn Glu Leu Ala Glu Lys Ala
                 165                 170                 175

Arg Asp Gly Lys Leu Thr Pro Gly Glu Met Lys Gly Ala Ser Cys Thr
             180                 185                 190

Ile Thr Asn Ile Gly Ser Ala Gly Gly Gln Trp Phe Thr Pro Val Ile
             195                 200                 205

Asn His Pro Glu Val Ala Ile Leu Gly Ile Gly Arg Ile Ala Glu Lys
210                 215                 220

Pro Ile Val Arg Cys Cys Glu Ile Val Ala Ala Pro Met Leu Ala Leu
225                 230                 235                 240

Ser Leu Ser Phe Asp His Arg Met Ile Asp Gly Ala Thr Ala Gln Lys
                 245                 250                 255

Ala Leu Asn His Ile Lys Arg Leu Leu Ser Asp Pro Glu Leu Leu Leu
             260                 265                 270

Met Glu Ala
     275

<210> SEQ ID NO 16
<211> LENGTH: 277
<212> TYPE: PRT
<213> ORGANISM: Bacillus stearothermophilus

<400> SEQUENCE: 16

Met Ser Tyr Ser Met Glu His Phe Arg Trp Gly Lys Pro Val Gly Gly
 1               5                  10                  15

Gly Ser Leu Ser Val Pro Gly Pro Ala Ala Glu Glu Lys Ala Ala
             20                  25                  30

Pro Ala Ala Ala Lys Pro Ala Thr Thr Glu Gly Glu Phe Pro Glu Thr
             35                  40                  45

Arg Glu Lys Met Ser Gly Ile Arg Arg Ala Ile Ala Lys Ala Met Val
 50                  55                  60

His Ser Lys His Thr Ala Pro His Val Thr Leu Met Asp Glu Ala Asp
65                  70                  75                  80

Val Thr Lys Leu Val Ala His Arg Lys Lys Phe Lys Ala Ile Ala Ala
                 85                  90                  95

Glu Lys Gly Ile Lys Leu Thr Phe Leu Pro Tyr Val Val Lys Ala Leu
             100                 105                 110

Val Ser Ala Leu Arg Glu Tyr Pro Val Leu Asn Thr Ser Ile Asp Asp

-continued

```
            115                 120                 125
Glu Thr Glu Glu Ile Ile Gln Lys His Tyr Tyr Asn Ile Gly Ile Ala
        130                 135                 140

Ala Asp Thr Asp Arg Gly Leu Leu Val Pro Val Ile Lys His Ala Asp
145                 150                 155                 160

Arg Lys Pro Ile Phe Ala Leu Ala Gln Glu Ile Asn Glu Leu Ala Glu
                165                 170                 175

Lys Ala Arg Asp Gly Lys Leu Thr Pro Gly Glu Met Lys Gly Ala Ser
            180                 185                 190

Cys Thr Ile Thr Asn Ile Gly Ser Ala Gly Gly Gln Trp Phe Thr Pro
        195                 200                 205

Val Ile Asn His Pro Glu Val Ala Ile Leu Gly Ile Gly Arg Ile Ala
    210                 215                 220

Glu Lys Pro Ile Val Arg Cys Cys Glu Ile Val Ala Ala Pro Met Leu
225                 230                 235                 240

Ala Leu Ser Leu Ser Phe Asp His Arg Met Ile Asp Gly Ala Thr Ala
                245                 250                 255

Gln Lys Ala Leu Asn His Ile Lys Arg Leu Leu Ser Asp Pro Glu Leu
            260                 265                 270

Leu Leu Met Glu Ala
            275
```

TARGETING OF MELANOCYTES FOR DELIVERING THERAPEUTIC OR DIAGNOSTIC AGENTS USING PROTEIN NANOCAGES

The Sequence Listing associated with this application is provided in text format in lieu of a paper copy, and is hereby incorporated by reference into the specification. The name of the text file containing the Sequence Listing is 690148_516D1_SEQUENCE LISTING.txt. The text file is 20.0 KB, was created on Nov. 12, 2021, and is being submitted electronically via EFS-Web.

FIELD OF THE INVENTION

The present invention relates generally to protein nanocages, pharmaceutical compositions containing them and methods for the treatment or diagnosis of hyperpigmentation disorders or other melanocyte-related disorders using said protein nanocages.

BACKGROUND OF THE INVENTION

Melanocytes are unique in that they produce eu-/pheomelanin pigments in unique membrane-bound organelles termed melanosomes, and are closely related to various diseases and disorders including hyperpigmentation disorders and melanoma.

It is known in the art that melanocytes produce melanin as a protective mechanism in response to the DNA damage induced by exposure to ultra violet (UV) radiation. However, hyper-expression of melanin in humans is known to result in pigmentation disorders such as melasma. Melasma occurs mostly on the face, occasionally on the neck, and rarely on the forearms. It predominantly affects females and has significant effect on psychology and quality of life due to its long-standing nature. Although the exact prevalence of melasma is unknown, it accounts for 0.25 to 4% of the patients seen in dermatology clinics in South East Asia (Bandyopadhyay D. Indian J Dermatol. 2009; 54 (4): 303-9). Topical treatments of melasma by inhibiting the tyrosinase enzymes responsible for melanin biosysthesis provide feasible options for the patients (Bandyopadhyay D. Indian J Dermatol. 2009; 54 (4): 303-9). However, current therapies suffer from complications such as irritation, depigmentation, exogenous ochronosis, stinging, allergic contact dermatitis and nail discoloration. One of the main reasons for these complications could be attributed to the untargeted delivery of drugs and active molecules to the affected areas (Paudel K S, et al. Ther Deliv. 2010 July; 1 (1): 109-31).

Therefore, there is still need in the art for alternative methods that overcome the drawbacks of existing techniques.

SUMMARY OF THE INVENTION

The present invention is directed to the aforementioned need in the art, and provides a melanocyte-targeting protein nanocage, a pharmaceutical composition comprising the nanocage, and methods for treating or diagnosing hyperpigmentation disorders or other melanocyte-related disorders using the nanocage or composition.

In one aspect, the present invention relates to a protein nanocage comprising a melanocyte-targeting moiety, wherein the melanocyte-targeting moiety is coupled to the exterior surface of the protein nanocage.

In various embodiments, the protein nanocage is composed of protein units selected from the group consisting of *Bacillus stearothermophilus* E2 protein of pyruvate dehydrogenase multi-enzyme complex (E2) having the amino acid sequence of SEQ ID NO:1, E2LC2 protein having the amino acid sequence of SEQ ID NO:2, *Archaeoglobus fulgidus* Ferritin (AfFtn) having the amino acid sequence of SEQ ID NO: 3, AfFtn-AA protein having the amino acid sequence of SEQ ID NO:4, *Homo sapiens* (Human) Ferritin (HsFtn) heavy chain having the amino acid sequence of SEQ ID NO: 5, HsFtn light chain having the amino acid sequence of SEQ ID NO:6, and variants, analogues and derivatives thereof.

In various embodiments, the melanocyte-targeting moiety is selected from the group consisting of the α-melanocyte stimulating hormone (α-MSH) peptide having the amino acid sequence of SEQ ID NO:7, the β-melanocyte-stimulating hormone (β-MSH) peptide having the amino acid sequence of SEQ ID NO:8, the γ-melanocyte-stimulating hormone (γ-MSH) peptide having the amino acid sequence of SEQ ID NO:9, the adrenocorticotropic hormone (ACTH) peptide having the amino acid sequence of SEQ ID NO:10, an antibody or aptamer specific for Melan-A (MLANA), Melanocortin-1 receptor (MC1R), Melanocortin-2 receptor (MC2R), Melanocortin-3 receptor (MC3R), Melanocortin-4 receptor (MC4R) or Melanocortin-5 receptor (MC5R), a variant, analogue or derivative thereof, and a combination thereof.

In various embodiments, the protein nanocage is coupled to or loaded with a therapeutic agent, a diagnostic agent or a combination thereof.

In certain embodiments, the diagnostic agent is an imaging agent.

In various embodiments, the protein nanocage further comprises a skin penetrating and cell permeating (SPACE) moiety coupled to the exterior surface of the protein nanocage, the SPACE moiety preferably being a peptide selected from the group consisting of ACTGSTQHQCG (SEQ ID NO:11), ACHSALTKHCG (SEQ ID NO:12), ACKTGSHNQCG (SEQ ID NO:13) and derivatives thereof. Further suitable SPACE moieties include, but are not limited to those, disclosed in international PCT application No. PCT/US2011/054967.

In certain embodiments, the exterior surface of the protein nanocage is functionalized with polyethylene glycol (PEG).

In various embodiments, the protein nanocage is used as a medicament or diagnostic agent.

In various embodiments, the protein nanocage is used in a method for treating or diagnosing hyperpigmentation disorders or other melanocyte-related disorders.

In another aspect, the invention is directed to a pharmaceutical composition comprising the protein nanocage and a pharmaceutically acceptable carrier.

In various embodiments, the pharmaceutical composition is used in a method for treating or diagnosing hyperpigmentation disorders or other melanocyte-related disorders.

In still another aspect, the invention encompasses a method for treating hyperpigmentation disorders or other melanocyte-related disorders in a subject, comprising administering to said subject an effective amount of the protein nanocage or pharmaceutical composition, the subject being a mammal, preferably a human.

In various embodiments, the compound or composition is topically administered.

In yet another aspect, encompassed in the invention is a method of diagnosing hyperpigmentation disorders or other melanocyte-related disorders in a subject, comprising administering to said subject an effective amount of the protein nanocage or pharmaceutical composition, the subject being a mammal, preferably a human.

In a final aspect, the invention concerns use of the protein nanocage or pharmaceutical composition in a method for treating or diagnosing hyperpigmentation disorders or other skin disorders.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
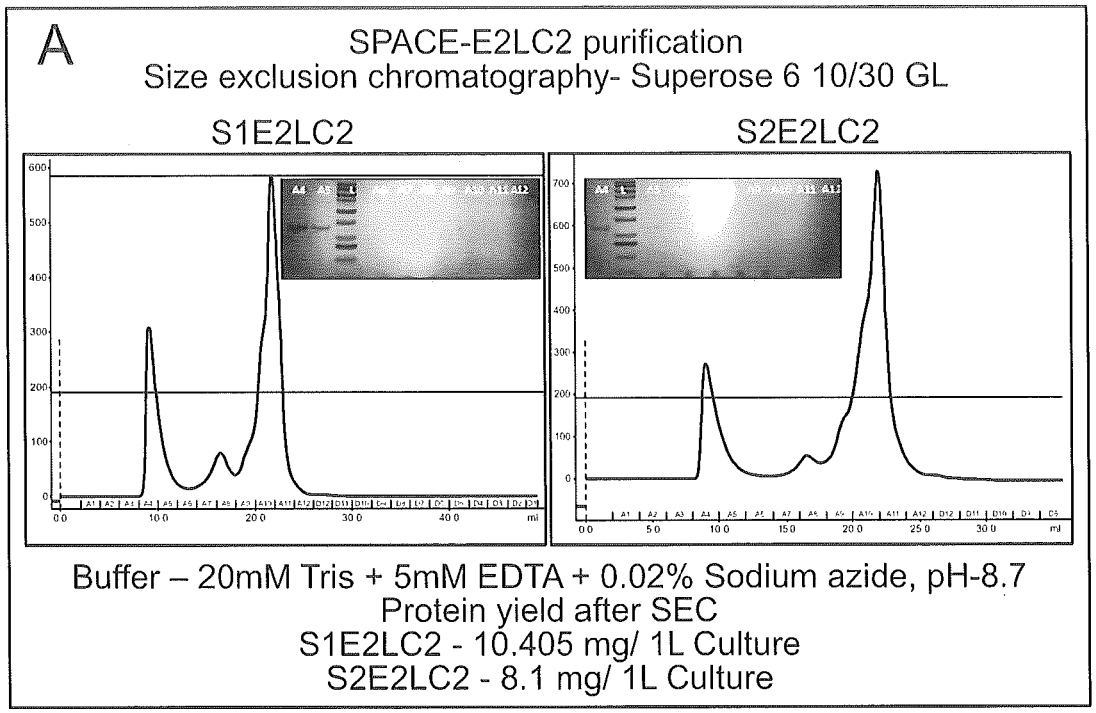
FIG. 1 shows purification and characterization of recombinantly expressed SPACE1-E2LC2 (S1LC2, SEQ ID NO:14), SPACE2-E2LC2 (S2LC2, SEQ ID NO: 15) and αMSH-E2LC2 (SEQ ID NO:16) proteins by size exclusion chromatography.
Figure 1:
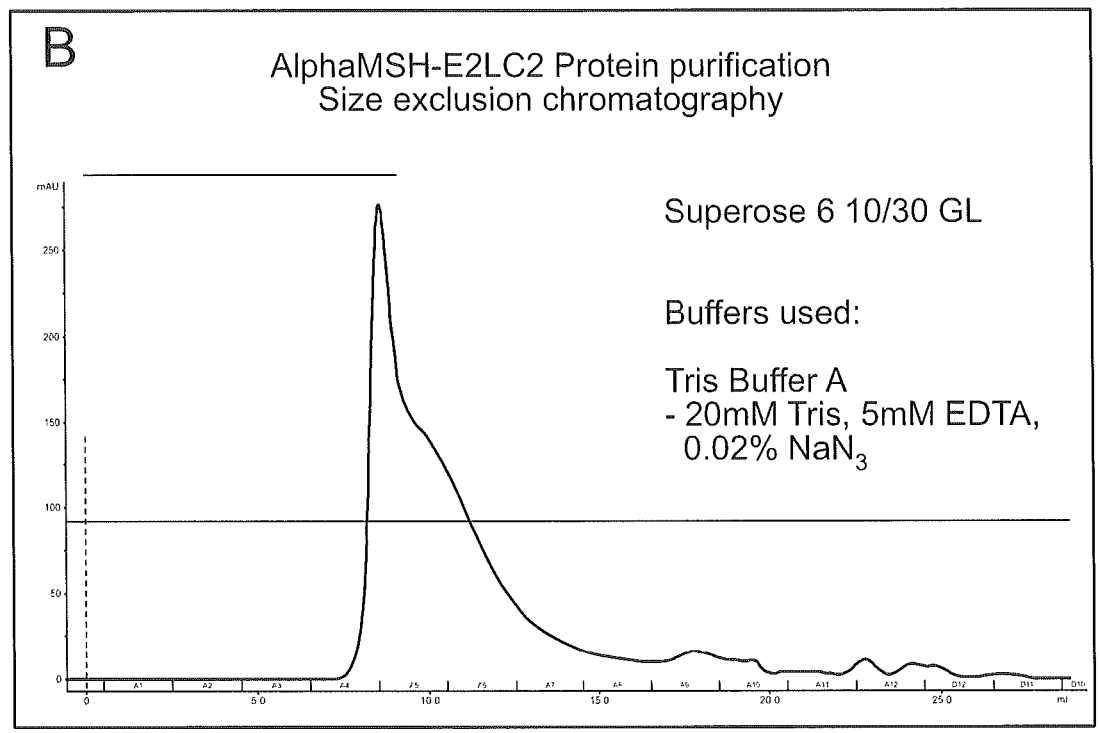

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. In case of conflict, the present document, including definitions, will control.

The object of the present invention is to provide a technique for melanocyte-targeted delivery of therapeutic and/or diagnostic agents. To this end, the present invention provides protein nanocages functionalized with melanocyte-targeting and drug delivery capabilities, taking advantage of the properties inherent to the protein nanocages as set forth below.

The rationale underlying the design of these protein nanocages is that by linking a melanocyte-targeting moiety to a protein nanocage carrying an agent, a nanoparticle for the delivery of the agent with improved melanocyte-targeting specificity and thus reduced side effects can be generated. Further modification of the protein nanocage may impart additional functionalities to the nanoparticle.

In one aspect, the present invention relates to a protein nanocage comprising a melanocyte-targeting moiety, wherein the melanocyte-targeting moiety is coupled to the exterior surface of the protein nanocage.

The articles "a" and "an" are used herein to refer to one or to more than one (i.e., to at least one) of the grammatical object of the article. By way of example, "an element" means at least one element and can include more than one element.

The term "protein nanocage", as used herein, refers to any cage-like structure with a constrained interior cavity assembled, preferably self-assembled, with precision from a predetermined number of subunits of any proteinaceous material. A wide range of self-assembling protein nanocages are employed by natural systems in a range of biological processes. For example, virus particles carry and deliver viral genomes to target cells, the protein ferritin sequesters iron for storage, and certain heat shock proteins encapsulate protein folding intermediates and chaperone their correct folding.

Protein nanocages, owing to their intrinsic properties, such as biodegradability, homogeneous size and shape, easy manipulation through rational design/genetic engineering, and facile scaling-up in large quantity, can be used to overcome some of the limitations found in traditional delivery vehicle such as liposomes.

It is to be understood that the protein nanocages of the present invention may be unmodified or modified. By "unmodified" herein is meant a protein nanocage that has not been genetically altered or modified by other physical, chemical, biochemical or genetic means. By "modified" herein is meant a protein nanocage that has been genetically altered or modified by a physical, chemical, biochemical or genetic means.

It is known in the art that the subunits of nanocages have distinct interfaces that can be synthetically exploited: the interior, the exterior, and the interface between subunits. The subunits that comprise the building blocks of the nanocages can be modified, e.g., chemically and/or genetically, to impart designed functionality to different surfaces. In this context, protein nanocages can serve as versatile platforms where multiple functional motifs can be added through genetic or chemical modifications.

In some embodiments, the protein nanocage is modified. Preferably, the modification results in protein nanocages with improved properties for use as delivery vehicles. For example, protein nanocages can be designed that are more stable than the unmodified cages or to contain binding sites for metal ions. Additionally, protein nanocages can be designed that have different charged interior surfaces for the selective entrapment and aggregation of therapeutic or diagnostic agents. Other modifications include the introduction of new chemical switches that can be controlled by pH or by redox conditions, the introduction of targeting moieties on the exterior surface, the addition of functional groups for the subsequent attachment of additional moieties, and covalent modifications.

The present invention contemplates a wide variety of protein nanocages. The nanocages may be derived from different sources and engineered to have various features.

In various embodiments, the protein nanocage is composed of protein subunits selected from the group consisting of *Bacillus stearothermophilus* E2 protein of pyruvate dehydrogenase multi-enzyme complex (E2) having the amino acid sequence of MLSVPGPAAAEEKAAPAAAKPATTEGEFPE-
TREKMSGIRRAIAKAMVHSKHTA
PHVTLMDEADVTKLVAHRKKFKAIAAEKGIKLT-
FLPYVVKALVSALREYPVLN TSIDDETEE- IIQKHYYNIGIAADTDRGLLVPVIKHADRKPI-FALAQEINELAEKAR DGKLTPGEMKGASCTIT-NIGSAGGQWFTPVINHPEVAILGIGRIAEKPIV-RDGEIV AAPMLALSLSFDHRMIDGATAQKALN-HIKRLLSDPELLLMEA (SEQ ID NO:1), E2LC2 protein having the amino acid sequence of
MLSVPGPAAAEEKAAPAAAKPATTEGEFPE-TREKMSGIRRAIAKAMVHSKHTA PHVTLMDEADVTKLVAHRKKFKAIAAEKGIKLT-FLPYVVKAL VSALREYPVLN TSIDDETEE-IIQKHYYNIGIAADTDRGLLVPVIKHADRKPI-FALAQEINELAEKAR DGKLTPGEMKGASCTIT-NIGSAGGQWFTPVINHPEVAILGIGRIAEKPIVRC-CEIV AAPMLALSLSFDHRMIDGATAQKALN-HIKRLLSDPELLLMEA (SEQ ID NO:2), *Archaeoglobus fulgidus* Ferritin (AfFtn) having the amino acid sequence of
MASISEKMVEALNRQINAEIYSAYLYLS-MASYFDSIGLKGFSNWMRVQWQEEL MHAMKMFDFVSERGGRVKLYAVEEPPSEWDSP-LAAFEHVYEHEVNVTKRIHE LVEMAMQEKD-FATYNFLQWYVAEQVEEEASAL-DIVEKLRLIGEDKRALLFLDK ELSLRQFTPPAEEEK (SEQ ID NO:3),
AfFtn-AA protein having the amino acid sequence of MASISEKMVEALNRQINAEIYSAYLYLS-MASYFDSIGLKGFSNWMRVQWQEEL MHAMKMFDFVSERGGRVKLYAVEEPPSEWDSP-LAAFEHVYEHEVNVTKRIHE LVEMAMQEKD-FATYNFLQWYVAEQVEEEASALDIVEKLRLIGE-DAAALLFLD KELSLRQFTPPAEEEK (SEQ ID NO:4),
*Homo sapiens* (Human) Ferritin (HsFtn) heavy chain having the amino acid sequence of MTTAST-SQVRQNYHQDSEAAINRQINLELYASYVYLSM-SYYFDRDDVALKNFA KYFLHQSHEERE-HAEKLMKLQNQRGGRIFLQDIKKPDCDDWESGL-NAMECAL HLEKNVNQSLLELHKLATDKNDPHLCDFIETH-YLNEQVKAIKELGDHVTNLRK MGAPESGLAEY-LFDKHTLGDSDNES (SEQ ID NO:5),
HsFtn light chain having the amino acid sequence of MSSQIRQNYSTDVEAAVNSLVNLYLQASY-TYLSLGFYFDRDDVALEGVSHFFR ELAEEKR-EGYERLLKMQNQRGGRALFQDIKKPAE-DEWGKTPDAMKAAMALE KKLNQALLDLHALGSARTDPHLCD-FLETHFLDEEVKLIKKMGDHLTNLHRLGG PEAGLGEYLFERLTLKHD (SEQ ID NO:6), and variants, analogues and derivatives thereof.

The term "variant", as used herein, refers to polymorphisms, i.e. the exchange, deletion, or insertion of one or more amino acids compared to the respectively indicated amino acid sequences. Particularly, protein homologues, i.e. those having at least 80% sequence identity to the respectively indicated amino acid sequences, as determined by the BLAST algorithm, are also encompassed in this concept. The term "analogue" may be used interchangeably with the term "mimetic", and refers to any synthetic structures which may or may not contain amino acids and/or peptide bonds but retain the structural and functional features of a nanocage polypeptide. The term "derivative", as used herein, refers to any entities modified by genetical, physical, chemical or biochemical means.

In preferred embodiments, the protein nanocage is *Bacillus stearothermophilus* E2 protein of pyruvate dehydrogenase multi-enzyme complex (E2), a self-assembled nanocage composed of 60 identical subunits, or is assembled from E2LC2 subunits having the amino acid sequence of SEQ ID NO:2.

The protein nanocage of the present invention also comprises a melanocyte-targeting moiety coupled to the exterior surface of the nanocage. In general, the targeting moiety is directed against and binds a target molecule, preferably a melanocyte-specific surface receptor or antigen, and allows the accumulation of the nanocage to melanocytes.

Thus, antibodies, aptamers, cell surface receptor ligands and hormones, and any other melanocyte-targeting chemical entities may be attached to the protein nanocage to bring it into close proximity to melanocytes.

In various embodiments, the melanocyte-targeting moiety comprised in the protein nanocage of the invention is selected from the group consisting of the α-melanocyte stimulating hormone (α-MSH) peptide having the amino acid sequence of SEQ ID NO:7, the β-melanocyte-stimulating hormone (β-MSH) peptide having the amino acid sequence of AEKKDEGPYRMEHFRWGSPPKD (SEQ ID NO:8), the γ-melanocyte-stimulating hormone (γ-MSH) peptide having the amino acid sequence of YVMGHFRW-DRFG (SEQ ID NO:9), the adrenocorticotropic hormone (ACTH) peptide having the amino acid sequence of SYS-MEHFRWGKPVGKKRRPVKVYPNGAEDESAEAFPLE (SEQ ID NO:10), an antibody or aptamer specific for Melan-A, Melanocortin-1 receptor (MC1R), Melanocortin-2 receptor (MC2R), Melanocortin-3 receptor (MC3R), Melanocortin-4 receptor (MC4R) or Melanocortin-5 receptor (MC5R), a variant, analogue or derivative thereof, and a combination thereof.

The term "antibody" includes antibody fragments, as are known in the art, including Fab, $Fab_2$, single chain antibodies (Fv for example), chimeric antibodies, single-chain antibodies, and fusion proteins including an antigen-binding portion of an antibody and a non-antibody protein, etc. In some embodiments, the antibody targeting moieties of the invention are humanized antibodies or human antibodies.

The term "antibody" includes antibodies of any isotype, fragments of antibodies which retain specific binding to antigen, including, but not limited to, Fab, Fv, scFv, and Fd fragments, chimeric antibodies, humanized antibodies, single-chain antibodies, fusion proteins including an antigen-binding portion of an antibody and a non-antibody protein, and non-immunoglobulin-based protein scaffolds as known in the art. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like.

Targeting moieties may be added to the surface of protein nanocages either by engineering protein nanocages to express the targeting moiety or by the addition of functional groups to the surface of the protein nanocage.

In a preferred embodiment, the protein nanocage is engineered to express the targeting moiety on the exterior surface thereof.

In a preferred embodiment, targeting moieties are added to the surface of protein nanocages through the use of functional groups. Functional groups may be added to the protein nanocage for subsequent attachment to additional moieties. Preferred functional groups for attachment are amino groups, carboxy groups, oxo groups and thiol groups.

These functional groups can then be attached, either directly or indirectly through the use of a linker. Linkers are well known in the art; for example, homo- or hetero-bifunctional linkers are well known (See 1994 Pierce Chemical Company catalog, technical section on cross-linkers, pages 155-200, as well as the 2003 catalog, both of which are incorporated herein by reference). Preferred linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and C2 alkene being especially preferred.

Any number of different agents, including organic, inorganic, and metalorganic agents, and mixtures thereof may be combined with the protein nanocages. The combination may be the loading of an agent into the interior space of the protein nanocage, and/or the attachment of an agent to one of the surfaces of the protein nanocages.

In various embodiments, the protein nanocage is coupled to or loaded with a therapeutic agent, a diagnostic agent or a combination thereof.

The term "therapeutic agent", as used herein, refers to any agent that can produce a therapeutic effect in a subject; the term "diagnostic agent", as used herein, refers to any agent that can produce a diagnostic signal detectable by any means in a subject.

The therapeutic or diagnostic agent of the invention may be a protein, nucleic acid molecule, compound, small molecule, organic compound, inorganic compound, or any other molecule with the desired properties suited for the practice of the present invention.

In certain embodiments, the diagnostic agent is an imaging agent.

The imaging agent can be any agent known to one of skill in the art to be useful for imaging a cell, tissue or a biofilm, preferably being a medical imaging agent. Examples of medical imaging agent include, but are not limited to, magnetic resonance imaging (MRI) agents, nuclear magnetic resonance imaging (NMR) agents, positron emission tomography (PET) agents, x-ray agents, optical agents, ultrasound agents and neutron capture therapy agents.

In some embodiments, the therapeutic or diagnostic agent is encapsulated within the protein nanocage, preferably during the assembly thereof, and therefore sequestered from the exterior environment by means of covalent, electrostatic and/or hydrophobic interactions with the inner surface of the assembled protein nanocage architecture.

In some embodiments, the therapeutic or diagnostic agent can be directly or indirectly coupled to the exterior surface through covalent, electrostatic and/or hydrophobic interactions.

In some embodiments, a surface of the protein nanocages is modified to allow for the attachment of functional groups that can be used to attach therapeutic and diagnostic agents. For example, replacement of amino acids on a surface of the nanocage by cysteine residues results in the presentation of reactive-SH groups, which can be reactive with bifunctional agents, such as maleimide to attach therapeutic and diagnostic agents to the nanocage. As another example, the protein nanocage can be engineered to display cationic peptides on the exterior surface to capture nucleotide molecules (e.g. DNA, RNA and derivatives thereof, including but not limited to siRNA) for delivery.

It should be appreciated that the therapeutic and diagnostic agents of the present invention may be attached to the protein nanocage via a linker. Linkers are well known in the art. Generally, suitable linker groups include, but are not limited to, alkyl and aryl groups, including substituted alkyl and aryl groups and heteroalkyl (particularly oxo groups) and heteroaryl groups, including alkyl amine groups, as defined above. Suitable linker groups include without limitation p-aminobenzyl, substituted p-aminobenzyl, diphenyl and substituted diphenyl, alkyl furan such as benzylfuran, carboxy, and straight chain alkyl groups of 1 to 10 carbons in length, short alkyl groups, esters, amide, amine, epoxy groups, nucleic acids, peptides and ethylene glycol and derivatives. In some other embodiments, the linkers include without limitation p-aminobenzyl, methyl, ethyl, propyl, butyl, pentyl, hexyl, acetic acid, propionic acid, aminobutyl, p-alkyl phenols, 4-alkylimidazole and polymers. The selection of the linker group is generally done using well-known molecular modelling techniques, to optimize the obstruction of the coordination site or sites of the metal ion. In addition, the length of this linker may be very important in order to achieve optimal results.

The protein nanocages of the present invention may include a payload release mechanism. The term "payload release mechanism", as used herein, refers to a mechanism by which the release of the therapeutic or diagnostic agent from the protein nanocage is controlled. Control of the release may be accomplished by controlling the opening and/or closing of the pores present in the protein nanocage or the integrity of the protein nanocage architecture itself. In one embodiment, the integrity of the protein nanocage architecture may be formulated such that the nanocage is sensitive to modification by various in vivo endogenous enzymes or other molecular cues such as the change of pH. The enzyme may be a hydrolase, the hydrolase preferably being a carbohydrase, lipase, or protease, for example, cathepsin or caspase.

In some embodiments, the protein nanocages include cleavable linkers for the release of the payload. For example, the present invention may provide a protein nanocage with a small molecule, the release of which is pH dependent. In one embodiment, the linker may be an acid labile linker, such as a hydrazone linkage. In another embodiment, a cleavable linker is incorporated into the small molecule covalently attached to the protein nanocage interior (See Flenniken, M. L. et al., 2005. *Chemical Comm.*: 447-449; Willner, D., et al., 1993. Bioconjug Chem 4:521-7). Other examples of acid labile linkers include linkers formed by using cis-aconitic acid, cis-carboxylic alkatriene, polymaleic anhydride, and other acid labile linkers, such as those linkers described in U.S. Pat. Nos. 5,563,250 and 5,505,931.

In one embodiment, the linker is a photo-labile linker. Examples of photo-labile linkers include those linkers described in U.S. Pat. Nos. 5,767,288 and 4,469,774, each of which is incorporated by reference in its entirety.

To address the challenge of poor skin penetration of macromolecules, the present invention contemplates coupling a skin penetrating and cell permeating moiety to the protein nanocage for skin melanocyte-targeted applications.

In various embodiments, the protein nanocage further comprises a skin penetrating and cell permeating (SPACE) moiety coupled to the exterior surface of the protein nanocage, the SPACE moiety preferably being a peptide selected from the group consisting of ACTGSTQHQCG (SEQ ID NO:11), ACHSALTKHCG (SEQ ID NO:12), ACKTGSHNQCG (SEQ ID NO:13) and derivatives thereof.

In certain embodiments, the exterior surface of the protein nanocage is functionalized with polyethylene glycol (PEG).

As used herein, PEG functionalization (i.e. PEGylation) refers to the modification of biological molecules by covalent or non-covalent conjugation with PEG, a non-toxic, non-immunogenic polymer, and is used as a strategy to overcome disadvantages associated with some biopharmaceuticals. It changes the physical and chemical properties of the biomedical molecule, such as its conformation, electrostatic binding, and hydrophobicity, and results in an improvement in the pharmacokinetic behavior of the drug. In general, PEGylation improves drug solubility and decreases immunogenicity. PEGylation also increases drug stability and the retention time in blood, and reduces proteolysis and renal excretion thereof, thereby allowing a reduced dosing frequency. The method for PEGylation is well known in the art.

It is to be understood that the protein nanocage may be further modified to be better suited for the practice of the present invention.

The nanocage polypeptides of the present invention may also be modified in a way to form chimeric molecules comprising a nanocage polypeptide fused to another heterologous polypeptide or amino acid sequence. In one embodiment, such a chimeric molecule comprises a fusion of a cage polypeptide with a tag polypeptide which provides an epitope to which an anti-tag antibody can selectively bind. The epitope tag is generally placed at the amino- or carboxyl-terminus of the polypeptide, although internal loops that are solvent exposed are also preferred. The presence of such epitope-tagged forms can be detected using an antibody against the tag polypeptide. Also, provision of the epitope tag enables the nanocage polypeptide to be readily purified by affinity purification using an anti-tag antibody or another type of affinity matrix that binds to the epitope tag. For example, poly-histidine tags make it possible to purify the protein nanocages or subunits thereof through nickel affinity chromatography. Various tag polypeptides and their respective antibodies are well known in the art.

Another type of modification of nanocages, if appropriate, comprises altering the native glycosylation pattern of the polypeptide. "Altering the native glycosylation pattern" is intended to generally mean deleting one or more carbohydrate moieties found in the native sequence of the nanocage subunits, and/or adding one or more glycosylation sites that are not present in the native sequence.

In various embodiments, the protein nanocage is used as a medicament or diagnostic agent.

In various embodiments, the protein nanocage is used in a method for treating or diagnosing hyperpigmentation disorders or other melanocyte-related disorders.

The terms "treating" and "treatment", as used herein, refer to reduction in severity and/or frequency of symptoms, elimination of symptoms and/or underlying cause, prevention of the occurrence of symptoms and/or their underlying cause, and improvement or remediation of damage.

It is known in the art that human melanocytes are distributed not only in the epidermis and in hair follicles but also in mucosa, cochlea (ear), iris (eye), and mesencephalon (brain) among other tissues. Melanocytes, which are derived from the neural crest, are unique in that they produce eu-/pheo-melanin pigments in unique membrane-bound organelles termed melanosomes, which can be divided into four stages depending on their degree of maturation. Pigmentation production is determined by three distinct elements: enzymes involved in melanin synthesis, proteins required for melanosome structure, and proteins required for their trafficking and distribution. Many genes are involved in regulating pigmentation at various levels, and mutations in many of them cause pigmentary disorders, which can be classified into three types: hyperpigmentation (including melasma), hypopigmentation (including oculocutaneous albinism [OCA]), and mixed hyper-/hypopigmentation (including dyschromatosis *symmetrica* hereditaria).

The term "hyperpigmentation disorders", as used herein, encompasses congenital hyperpigmentation disorders include those involving epidermal hyperpigmentation (nevus cell nevus, Spitz nevus, and nevus *spilus*), dermal hyperpigmentation (blue nevus, nevus Ohta, dermal melanosis, nevus Ito, and Mongolian spot), ephelides, acropigmentation *reticularis*, Spitzenpigment/acropigmentation, and lentiginosis (generalized lentiginosis, LEOPARD syndrome, inherited patterned lentiginosis, Carney complex, Peutz-Jeghers syndrome, Laugier-Hunziker-Baran syndrome, and Cronkhite-Canada syndrome), and acquired hyperpigmentation disorders including senile lentigines/lentigo, melasma/chloasma, Riehl's melanosis, labial melanotic macule, penile/vulvovaginal melanosis, erythromelanosis *follicularis* faciei Kitamura, UV-induced pigmentation (tanning and pigmentation *petaloides* actinica), postinflammatory pigmentation (friction melanosis and ashy dermatosis), chemical/drug-induced pigmentation, pigmentary demarcation lines (Yamaguchi and Hearing. Cold Spring Harb Perspect Med. 2014 May 1; 4 (5)). Hyperpigmentation may be caused by either increased melanin production by existing melanocytes or proliferation of active melanocytes.

The term "other melanocyte-related disorders", as used herein, refers to any disorders or diseases caused by the pathogenesis of melanocytes other than hyperpigmentation disorders, including without limitation hypopigmentation disorders and melanoma (See Yamaguchi and Hearing. Cold Spring Harb Perspect Med. 2014 May 1; 4 (5), which is incorporated by reference in its entirety).

In some embodiments, for the treatment of hyperpigmentation disorders the protein nanocage can possibly carry hydroquinone (dihydroxybenzene), azelaic acid, kojic acid, retinoids, corticosteroids, glycolic acid, mequinol, arbutin, tranexamic acid, metformin, niacinamide, siRNA to Microphthalmia-Associated Transcription Factor (MITF) or tyrosinase, or a combination thereof.

In some embodiments, the protein nanocage of the present invention is used for the specific delivery of DNA, RNA or protein coupled to or loaded in the nanocage into melanocytes in vivo or in vitro.

In another aspect, the invention is directed to a pharmaceutical composition comprising the protein nanocage and a pharmaceutically acceptable carrier.

The term "pharmaceutically acceptable" is employed herein to refer to those materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically-acceptable carrier" as used herein means a pharmaceutically-acceptable material, composition or vehicle, such as a liquid or solid filler, diluent, excipient, or solvent encapsulating material, involved in carrying or transporting the subject extract from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth;

malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; sterile distilled water; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. See *Remington: The Science and Practice of Pharmacy*, 19th Ed. (Easton, Pa.: Mack Publishing Co., 1995), which discloses typical carriers and conventional methods of preparing pharmaceutical formulations.

Wetting agents, emulsifiers and lubricants, such as sodium lauryl sulfate and magnesium stearate, as well as coloring agents, release agents, coating agents, and perfuming agents, preservatives and antioxidants can also be present in the compositions.

In various embodiments, the pharmaceutical composition is used in a method for treating or diagnosing hyperpigmentation disorders or other melanocyte-related disorders. It is to be noted that compositions for cosmetic applications are also within the scope of the present invention.

Prior to being used in the treatment or diagnosis, pharmaceutical formulations composed of one or more of the protein nanocages in association with a pharmaceutically acceptable carrier may need to be formulated. Proper formulation is dependent upon the route of administration chosen.

In the preferred embodiments, the pharmaceutical compositions of the present invention are specially formulated for administration in solid or liquid form for topical application, for example, as a emulsion, cream, ointment, drops, gels, or a controlled-release patch or spray or sustained-release formulation applied to the skin, for example, as a cream or foam. Suitable carrier components include, but are not limited to, mineral oil, sorbitan monostearate, polysorbate 60, cetyl esters wax, cetearyl alcohol, 2-octyldodecanol, benzyl alcohol, liquid petroleum, white petroleum, propylene glycol, polyoxyethylene polyoxypropylene compound, emulsifying wax and water.

In other embodiments, the pharmaceutical compositions of the present invention are formulated for administration in other routes including, without limitation, depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy*, cited above.

In still another aspect, the invention encompasses a method for treating hyperpigmentation disorders or other melanocyte-related disorders in a subject, comprising administering to said subject an effective amount of the protein nanocage or pharmaceutical composition, the subject being a mammal, preferably a human.

By the terms "effective amount" of a nanocage of the invention is meant a nontoxic but sufficient amount of the nanocage to provide the desired effect.

In various embodiments, the compound or composition is topically administered.

In yet another aspect, encompassed in the invention is a method of diagnosing hyperpigmentation disorders or other melanocyte-related disorders in a subject, comprising administering to said subject an effective amount of the protein nanocage or pharmaceutical composition, the subject being a mammal, preferably a human. The detection means and instruments are well known in the art.

One skilled in the art would readily appreciate that the functionalization and formulation of protein nanocages for the practice of the present invention should be tailored to the pathogenesis of interest. For example, for the treatment or diagnosis of skin hyperpigmentation disorders, a skin penetrating and cell permeating moiety coupled to the exterior surface of the nanocages may be essential. As another example, protein nanocages may have to be differentially configured for use in the treatment or diagnosis of primary melanoma and metastasized melanoma, due to their different locations within the body or differing expression of melanocyte-specific antigens selected for targeting.

The skilled artisan would also realize that the proper route and mode of administering the protein nanocage or pharmaceutical composition to a subject should be determined on a case-by-case basis.

In a final aspect, the invention concerns use of the protein nanocage or pharmaceutical composition in a method for treating or diagnosing hyperpigmentation disorders or other skin disorders.

The present invention is further illustrated by the following examples. However, it should be understood, that the invention is not limited to the exemplified embodiments.

EXAMPLES

Example 1: Construction of Plasmids Encoding SPACE1-E2LC2, SPACE2-E2LC2 and αMSH-E2LC2 Fusion Proteins The amino acid sequences of SPACE1-E2LC2 (S1LC2; SEQ ID NO:14), SPACE2-E2LC2 (S2LC2; SEQ ID NO:15) and αMSH-E2LC2 (SEQ ID NO:16) fusion proteins were codon optimized using a tool from Integrated DNA Technologies, Inc (http://eu.idtdna.com/CodonOpt). The pSMART plasmids encoding said fusion proteins were purchased from the same company and digested by NdeI and BamHI restriction enzymes. Subsequently, the DNA fragments encoding the fusion proteins were purified and subcloned into the pET11a plasmid. *Escherichia coli*-DH5α and *Escherichia coli*-BL21 (DE3) competent cells were then transformed with the ligated plasmids and plated in LB agar plates supplemented with ampicillin (100 mg/mL) and incubated at 37° C. for 16 hours. Single clones from *E. coli* BL21 (DE3) agar plates were isolated and inoculated in 20 mL LB medium as the starter culture before being transferred to 1 L cultures for large scale production of the fusion proteins.

Example 2: Production and Characterization of Protein Nanocages

Figure 2:
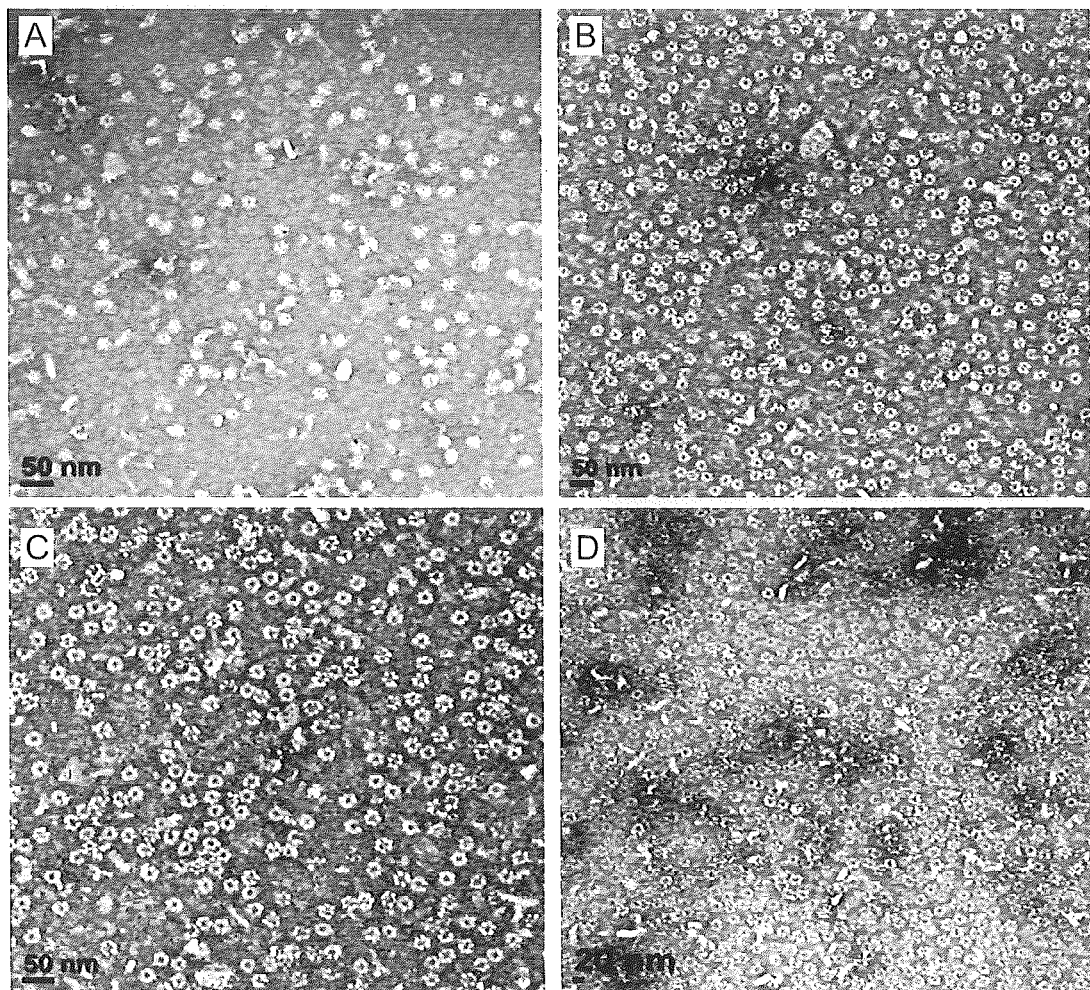
FIG. 2 shows TEM images of E2LC2 (SEQ ID NO:2; A), S1LC2 (B), S2LC2 (C) and αMSH-E2LC2 (D).

Protocols for the production and purification of E2 protein used in the present application had been previously reported (Dalmau M, et al. Biotechnol Bioeng. 2008 Nov. 1; 101 (4): 654-64). *E. coli* BL21 (DE3) cells were transformed with pET11a plasmids encoding E2LC2, S1LC2, S2LC2 or αMSH-LC2. The 20 ml starter culture of cells were grown overnight and inoculated in 1 L of LB medium. The cells were treated with 1 mM IPTG to overexpress the proteins when the OD value reached 0.6-0.8. After 4 hours cells were harvested by centrifugation at 4,700 g for 30 minutes. Harvested cells were resuspended in a buffer (20 mM Tris, 5 mM EDTA and 0.02% sodium azide) and ultrasonicated by Vibracell VC 750 Ultrasonic Cell Disrupter at 37% amplitude for 20 minutes with pulse on and off for 5 seconds. The sonicated solution was heat-treated at 75° C. for 15 minutes and was ultracentrifuged at 193,011 g for 1 hour. The supernatant was then collected and subjected to purification by fast protein liquid chromatography (FPLC) by ion exchange chromatography using the Hi Prep QFF 16/10 column. The flow-through fractions were analyzed by SDS PAGE for purity. The pooled protein fractions were concentrated to 2 mg/ml by Amicon 100-kDa centrifugal cut-off filters. The concentrated protein samples were then injected into the size exclusion chromatographic column Superose 6 10/300GL as shown in FIG. 1. The elution buffer used comprised 20 mM Tris, 5 mM EDTA and 0.02% sodium azide. The purity of the protein solutions was tested by SDS-PAGE. Purified proteins were then characterized for size, hydrodynamic diameter and self-assembly by mass spectrometry, dynamic light scattering (DLS) and transmission electron microscopy (TEM), respectively. For TEM analysis, the protein samples were added to a copper grid, dried for 10-15 minutes and the dried portion of the grid was stained with 1.5% uranyl acetate and dried for 15 minutes. The stained samples were then subjected to TEM analysis. As shown in FIG. 2, the TEM analysis clearly confirmed the successful self-assembly of the recombinantly expressed proteins into nanocage structures.

Figure 3:
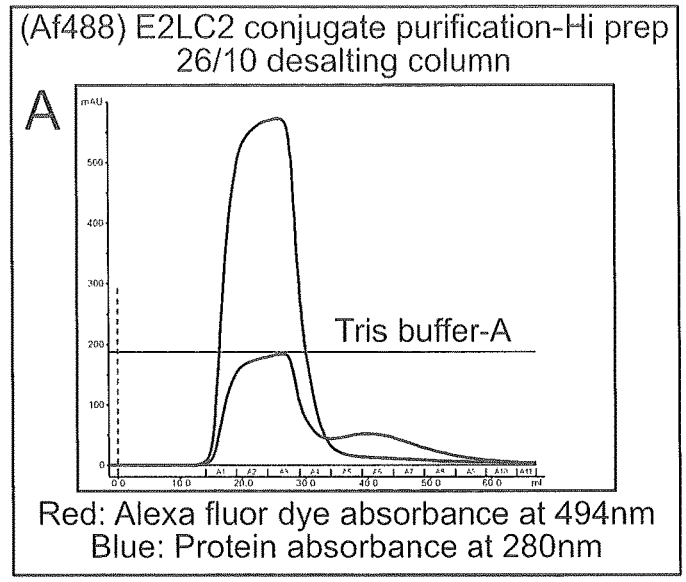
FIG. 3 shows purification of Alexa Fluor 488-conjugated E2LC2 (A), S1LC2 (B) and S2LC2 (C) by gel filtration chromatography.
Figure 3:
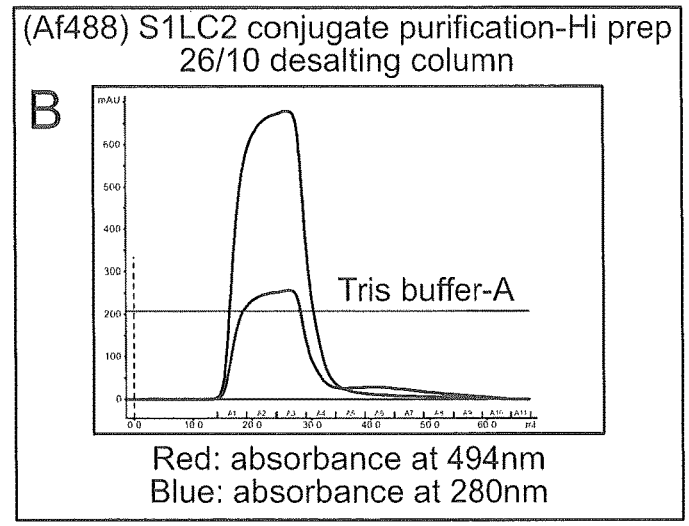
Figure 3:
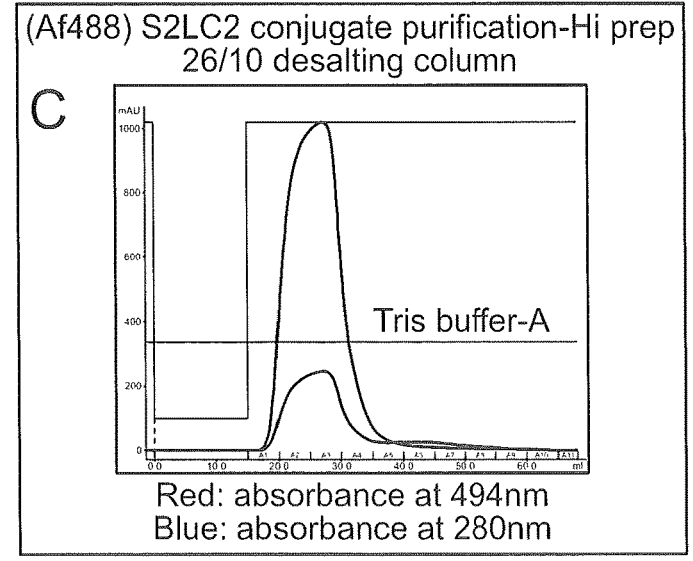

Example 3: Conjugation of Protein Nanocages with Alexa Fluor 488 Fluorescent Dye The purified proteins were conjugated with thiol reactive Alexa Fluor 488 (AF488) dye for convenience of detection and quantification. The E2LC2, S1LC2, S2LC2 and αMSH-LC2 protein nanocages were incubated with 10 mM excess tris carboxy ethyl phosphine (TCEP) for 1 hour to reduce the 120 cysteine residues residing inside the protein nanocages. The reduced proteins were reacted with 50 molar excess of Alexa Fluor 488 dye at room temperature for 2 hours and subsequently at 4° C. for 20 hours at pH 7.0. After the conjugation reaction, the dye-conjugated protein nanocages were purified by gel filtration chromatography using Hi prep 26/10 desalting column by FPLC. The samples were spun down at 12,000 g for 15 minutes after the conjugation reaction. The pellet fraction was discarded and the supernatant was collected and loaded onto the desalting column with elution buffer (20 mM Tris, 5 mM EDTA and 0.02% sodium azide at pH 7.0). The protein-dye conjugate was eluted out around A1 to A3 fractions as shown in FIG. 3. The protein samples were pooled together in a 50 ml falcon tube and covered in aluminium foil to be protected from light The amount of protein was determined using BCA assay and the samples were used in subsequent experiments Example 4: Cell Penetration by SPACE-E2LC2 Protein Nonocages Primary epidermal melanocytes (CC-2586) were purchased and cultured from passage 1 to passage 4.

Figure 4:
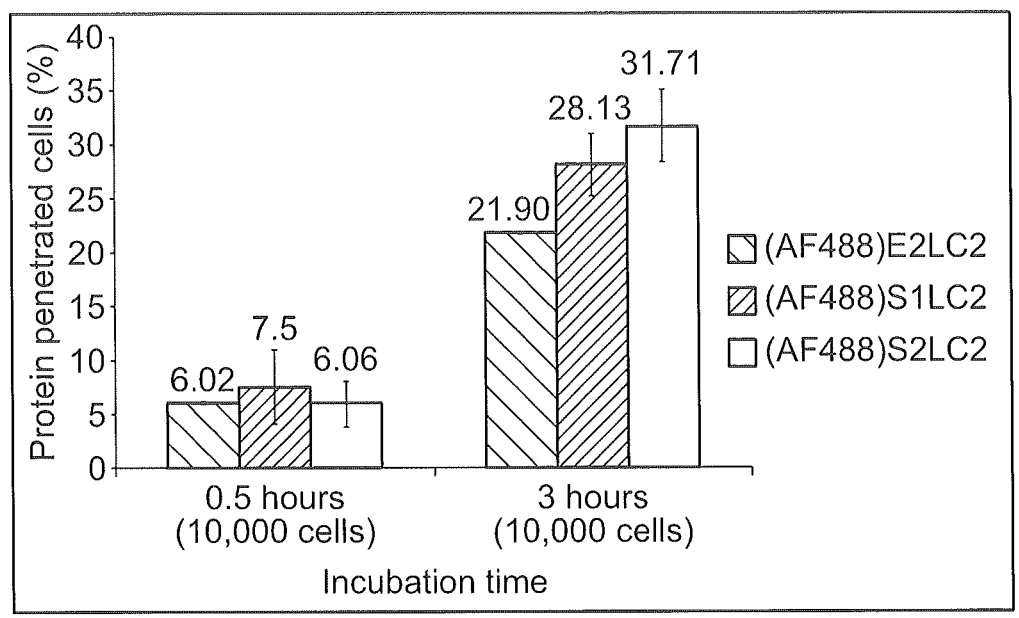
FIG. 4 shows flow cytometric analysis of primary epidermal melanocytes stained with Alexa Fluor 488-conjugated E2LC2, S1LC2 and S2LC2 protein nanocages for 0.5 or 3 hours.

For flow cytometric analysis, melanocytes from passage 2 were seeded in 6-well plates (9.6 cm2 per well) and allowed to reach 90% confluence and treated with E2LC2, S1LC2, S2LC2 proteins at 10 μg/ml for 0.5 or 3 hours. After the incubation, the medium was aspirated and the cells were washed with PBS. The cells were detached by 0.05% trypsin-EDTA and collected into 15 ml falcon tubes. The cells were then fixed with 4% paraformaldehyde for 10 minutes, followed by three times of washing with PBS. The samples were then resuspended in PBS and subjected to flow cytometric analysis by BD Fortessa X20 cell cytometer as shown in FIG. 4.

Example 5: Enhanced Targeting of Melanocytes Mediated by the αMSH Peptide

Figure 5:
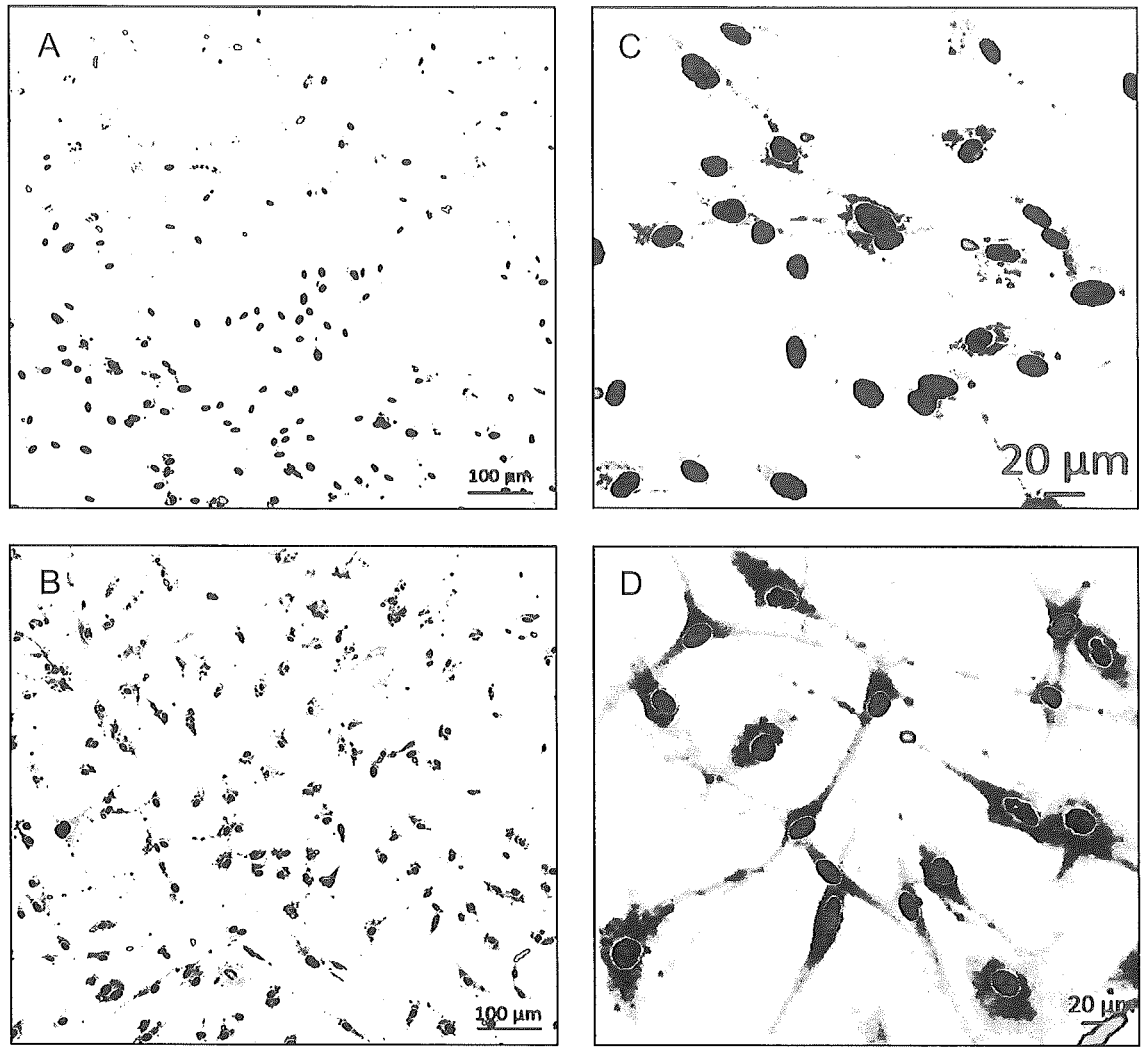
FIG. 5 shows confocal imaging analysis of primary epidermal melanocytes stained with Alexa Fluor 488-conjugated E2LC2 (A, C) or Alexa Fluor 488-conjugated αMSH-E2LC2 (B, D) protein nanocages. Cell nuclei were stained with Nuc blue stain.

For confocal imaging analysis, melanocytes from passage 2 were seeded in 8-well confocal chambers and allowed to grow as a monolayer till 70-80% confluence. Cells were further incubated with AF488-conjugated E2LC2 (50 μg/ml) or AF488-conjugated αMSH-E2LC2 (50 μg/ml) nanocages for 2 hours. After the incubation period, the medium was aspirated and the cells were washed with PBS. Cell nuclei were stained with Nuc blue stain, and the cells were fixed with 4% paraformaldehyde for 10 minutes, followed by washing with PBS for 3 times. The samples were then imaged using a confocal microscope. As shown in FIG. 5, αMSH peptide functionalization of the nanocage significantly enhanced the melanocyte-targeting capability thereof.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A protein nanocage comprising a melanocyte-targeting moiety and a skin penetrating and cell permeating (SPACE) moiety, wherein the melanocyte-targeting moiety and the skin penetrating and cell permeating (SPACE) moiety are coupled directly to the exterior surface of the protein nanocage, and wherein
   (a) the protein nanocage is composed of protein units selected from the group consisting of *Archaeoglobus fulgidus* Ferritin (AfFtn) having the amino acid sequence of SEQ ID NO:3, AfFtn-AA protein having the amino acid sequence of SEQ ID NO:4, *Homo sapiens* (Human) Ferritin (HsFtn) heavy chain having the amino acid sequence of SEQ ID NO:5, and HsFtn light chain having the amino acid sequence of SEQ ID NO:6, and
   (b) the melanocyte-targeting moiety is selected from the group consisting of
      (i) α-melanocyte-stimulating hormone (α-MSH) peptide,
      (ii) β-melanocyte-stimulating hormone (β-MSH) peptide,
      (iii) γ-melanocyte-stimulating hormone (γ-MSH) peptide,
      (iv) adrenocorticotropic hormone (ACTH) peptide, and
      (v) a combination of any two or more of (i) to (iv),
   wherein the α-melanocyte-stimulating hormone (α-MSH) peptide has the amino acid sequence of SEQ ID NO:7, the β-melanocyte-stimulating hormone (β-MSH) peptide has the amino acid sequence of SEQ ID NO:8, the γ-melanocyte-stimulating hormone (γ-MSH) peptide has the amino acid sequence of SEQ ID NO:9, and the adrenocorticotropic hormone (ACTH) peptide has the amino acid sequence of SEQ ID NO: 10; and
   (c) the SPACE moiety is a peptide selected from the group consisting of ACTGSTQHQCG (SEQ ID NO:11), ACHSALTKHCG (SEQ ID NO:12), and ACKTGSHNQCG (SEQ ID NO:13).

2. The protein nanocage of claim 1, wherein the protein nanocage is coupled to or loaded with a therapeutic agent, a diagnostic agent or a combination thereof.

3. The protein nanocage of claim 2, wherein the diagnostic agent is an imaging agent.

4. The protein nanocage of claim 1, wherein the exterior surface of the protein nanocage is functionalized with polyethylene glycol (PEG).

5. The protein nanocage of claim 1 for use as a medicament or diagnostic agent, wherein the protein nanocage is coupled to or loaded with a therapeutic agent, or a diagnostic agent, respectively.

6. The protein nanocage of claim 1 for use in a method for treating or diagnosing hyperpigmentation disorders or other melanocyte-related disorders, wherein the protein nanocage is coupled to or loaded with a therapeutic agent or a diagnostic agent, respectively.

7. A pharmaceutical or cosmetic composition comprising a protein nanocage of claim 1, wherein the protein nanocage is coupled to or loaded with a therapeutic agent, or a diagnostic agent, respectively.

8. The pharmaceutical or cosmetic composition of claim 7 for use in a method for treating or diagnosing hyperpigmentation disorders or other melanocyte-related disorders.

9. A method for treating or diagnosing hyperpigmentation disorders or other melanocyte-related disorders in a subject, comprising administering to said subject an effective amount of a protein nanocage of claim 1 or a pharmaceutical or cosmetic composition comprising the protein nanocage of claim 1 and a pharmaceutically acceptable carrier, the subject being a mammal, wherein the protein nanocage is coupled to or loaded with a therapeutic agent, or a diagnostic agent, respectively.

10. The method of claim 9, wherein the protein nanocage or the pharmaceutical or cosmetic composition is topically administered for the treatment of hyperpigmentation disorders or other melanocyte-related disorders.

11. The method of claim 9, wherein the subject is a human.

* * * * *